United States Patent [19]
Guadliana et al.

[11] Patent Number: 5,849,730
[45] Date of Patent: Dec. 15, 1998

[54] PROCESS FOR PREPARING DEMETHYLRAPAMYCINS

[75] Inventors: Mark A. Guadliana, Stonington, Conn.; Susan J. Truesdell, Warwick, R.I.

[73] Assignee: Pfizer Inc., New York, N.Y.

[21] Appl. No.: 765,438

[22] PCT Filed: Jul. 10, 1995

[86] PCT No.: PCT/IB95/00548

§ 371 Date: Jan. 16, 1997

§ 102(e) Date: Jan. 16, 1997

[87] PCT Pub. No.: WO96/06847

PCT Pub. Date: Mar. 7, 1996

Related U.S. Application Data

[63] Continuation of Ser. No. 298,881, Aug. 31, 1994, abandoned.

[51] Int. Cl.$^6$ ............... C07D 498/18; A61K 31/445
[52] U.S. Cl. ............................. 514/183; 540/456
[58] Field of Search ............... 540/456; 514/183

[56] References Cited

U.S. PATENT DOCUMENTS

| | | | |
|---|---|---|---|
| 3,929,992 | 12/1975 | Sehgal | 424/122 |
| 4,316,885 | 2/1982 | Rakhit | 424/122 |
| 4,981,792 | 1/1991 | Ihamine et al. | 435/119 |
| 5,091,389 | 2/1992 | Oneydaka | 514/291 |
| 5,100,899 | 3/1992 | Calne | 514/291 |
| 5,283,257 | 2/1994 | Gregory et al. | 514/458 |
| 5,286,730 | 2/1994 | Caufield | 514/291 |
| 5,321,009 | 6/1994 | Baeder et al. | 514/4 |
| 5,387,680 | 2/1995 | Nelson | 540/456 |
| 5,525,610 | 6/1996 | Caufield et al. | 514/291 |
| 5,540,931 | 7/1996 | Hewitt et al. | 424/434 |

FOREIGN PATENT DOCUMENTS

| | | |
|---|---|---|
| 0396399 | 5/1990 | European Pat. Off. |
| 0467606 | 1/1992 | European Pat. Off. |
| 514 144 | 11/1992 | European Pat. Off. |
| WO 9316189 | 8/1993 | WIPO |
| WO 94/02136 | 2/1994 | WIPO |
| WO 9412655 | 6/1994 | WIPO |
| WO 9418208 | 8/1994 | WIPO |
| WO 92/26265 | 11/1994 | WIPO |

OTHER PUBLICATIONS

Vezina, *J. Antibiotics*, 1975, 28, 721–726.
Chen, *J. Antibiotics*, 1992, 45, 118–123.
Morris, *Med. Sci. Res.*, 1989, 17, 877.
Strauch, *FASEB*, 1989, 3, 3411.
Stepkowski, *Transplantation Proceedings*, 1991, 23, 507–508.

*Primary Examiner*—Mukund J. Shah
*Assistant Examiner*—Bruck Kifle
*Attorney, Agent, or Firm*—Peter C. Richardson; Gregg C. Benson; Robert T. Ronau

[57] ABSTRACT

A compound of the formula (IV)

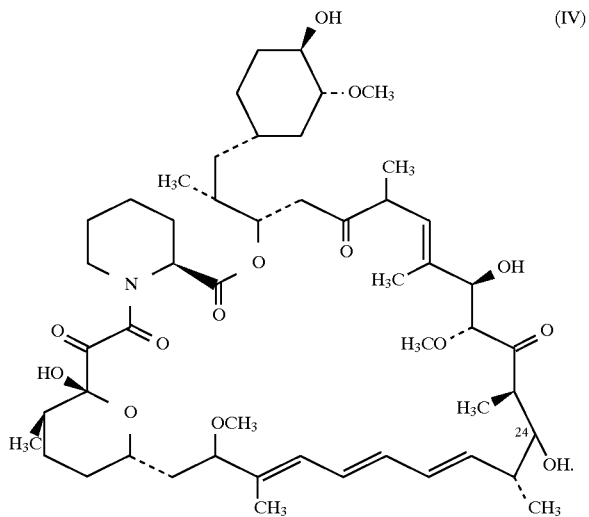

and a process for preparing the compound of formula (IV). Also disclosed is a process for preparing C-16-demethylrapamycin and C-39-demethylrapamycin. The process of this invention comprises fermenting Actinoplanes sp. ATCC 63771 in the presence of rapamycin and isolating the products produced thereby.

4 Claims, No Drawings

PROCESS FOR PREPARING DEMETHYLRAPAMYCINS

This application is the national stage of International application number PCT/IB95/00548, filed Jul. 10, 1995, entitled Process for Preparing Demethylrapamycins, which is a continuation of U.S. application Ser. No. 08/298,881, filed Aug. 31, 1994, now abandoned.

BACKGROUND OF THE INVENTION

The present invention relates to the field of immunosuppressant macrolides and to processes for preparing demethyl derivatives of rapamycin from rapamycin. The process comprises fermenting the microorganism Actinoplanes sp. ATCC 53771 in the presence of rapamycin.

Rapamycin is an antifungal and immunosuppressant compound having the structure of formula (I),

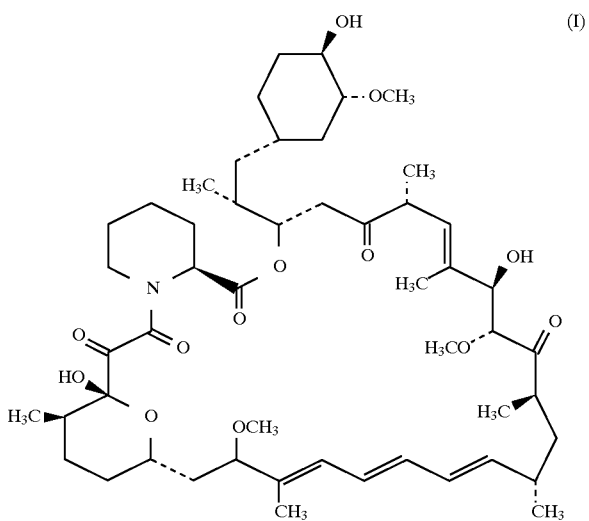

(I)

which can be prepared by fermenting *Streptomyces hygroscopicus*. Rapamycin has been reported to be effective in models for allergic encephalomyelitis, multiple sclerosis, adjuvant rheumatoid arthritis and inhibition of the formation of IgE-like antibodies. Rapamycin has been shown to prolong the survival time of organ grafts in histoincompatible rodents. R. Morris, Med. Sci. Res., 1989, 17, 877. Rapamycin has been shown to inhibit T-cell activation. Strauch, FASEB, 3, 3411, 1989.

Rapamycin has been shown to be useful in combination with Cyclosporin A. This combination has the advantage of reducing the amount of Cyclosporin A required to produce an immunosuppressant effect when given to heart, kidney, bowel, pancreas or other transplant patients. This effectively reduces the nephrotoxicity inherent in Cyclosporin A treatment. Stepkowski, S. M. et al., Transplantation Proceedings, 23,507–08, 1991.

Derivatives of rapamycin have also been reported to have antifungal activity. Additionally, various rapamycin derivatives have been reported to be useful in the treatment of transplantation rejection, host vs. graft disease, autoimmune diseases, diseases of inflammation, solid tumors, and fungal infections. Failli, EP 0 467 606 and Oneydaka, U.S. Pat. No. 5,091,389. C-16 and C-39 demethylrapamycin have themselves been reported to have this activity.

Actinoplanes sp. ATCC 53771, when fermented in the presence of FK520 and FK506, which are also macrolides, has been shown to produce various demethylated analogs of FK520 and FK506. Chen et al., Journal of Antibiotics, 1992, 45, 118–123.

This invention relates to an improved process for the preparation of C-16 and C-39 demethylrapamycin as well as the preparation of C-24 hydroxyrapamycin. This process involves fermenting Actinoplanes sp. ATCC 53771 in the presence of rapamycin to produce C-16 and C-39 demethylrapamycin as well as C-24 hydroxyrapamycin.

SUMMARY OF THE INVENTION

This invention relates to a process for preparing compounds of the formulae

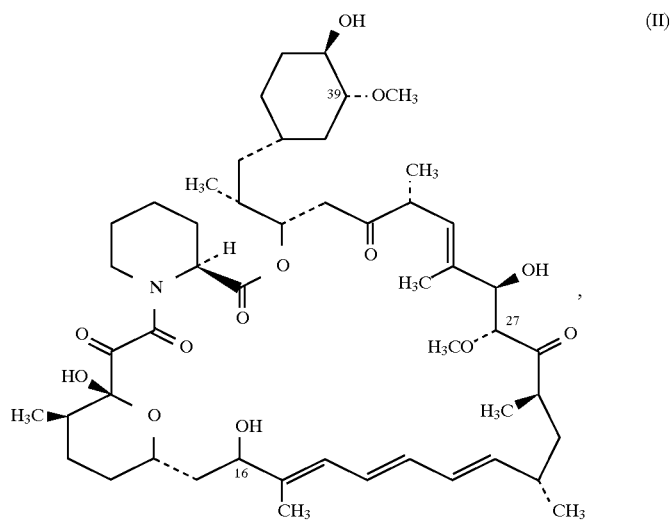

(II)

-continued

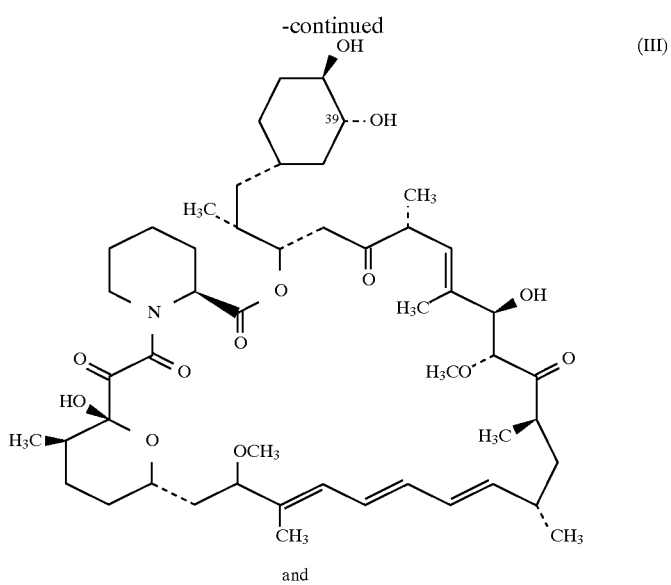

(III)

and

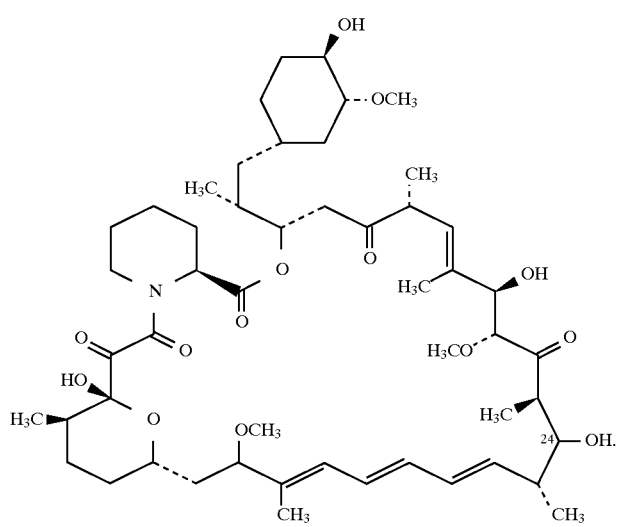

(IV)

This invention also relates to the compound of the formula (IV) above, which has antifungal activity. Hence this compound can be used to treat or prevent infections in mammals caused by fungi. Accordingly, this invention embraces a method of treating diseases caused by a fungus in a mammal in need of such treatment comprising administering to said mammal an effective amount of the compound of formula (IV) or a pharmaceutically acceptable salt thereof.

Additionally, this invention embraces a pharmaceutical composition comprising the compound of formula (IV) and a pharmaceutically acceptable carrier.

DETAILED DESCRIPTION OF THE INVENTION

The process of this invention is readily carried out. Thus, Actinoplanes sp. ATCC 53771 is fermented in the presence of rapamycin to microbially modify rapamycin, producing C-16-demethylrapamycin, C-39-demethylrapamycin and C-24-hydroxyrapamycin.

A lyophilized sample of Actinoplanes sp. ATCC 53771 was deposited with the American Type Culture Collection, 12301 Parklawn Drive, Rockville, Md., 20852, U.S.A., under the terms of the Budapest Treaty on 8 Jun. 1994. This newly deposited culture was given the new deposit number of ATCC 55586. All restrictions on the availability to the public of the microorganism culture so deposited will be irrevocably removed upon the issuance of a patent from this specification.

Cultures of Actinoplanes sp. ATCC 55586 can be obtained from the American Type Culture Collection. A culture so obtained is added to a suitable growth medium and is incubated with shaking until growth occurs. The cultures thus prepared are used to inoculate slants. Portions of these slants are frozen as master stocks. Actinoplanes sp. ATCC 55586 is inoculated from slants into two flasks containing a growth medium whose composition is shown below. The fermentation is carried out at temperatures ranging from about 22 to about 32; however, for optimum results it is preferable to conduct the fermentation at about 28. The pH of the medium is controlled at about pH 6–7 by the use of suitable organic or inorganic buffers incorporated into the fermentation medium or by periodic addition of a base. Good growth of the microorganism is achieved within 48 to 72 hours. The contents of the flasks are transferred to a Fernbach flask containing fresh growth medium having the same composition as the previously used growth medium. Variation of the medium will alter the yield of the compound and its rate of production. The preferred media composition is set forth in the example section. After shaking for one additional day, a sterile-filtered solution of rapamycin in a suitable solvent such as dimethyl sulfoxide or dimethylformamide is added. The fermentation is continued for one to six days. It is preferred to continue the fermentation for about two days.

A suitable growth medium for use in the process of this invention will contain a source or sources of assimilable carbon, assimilable nitrogen and inorganic salts containing essential minerals. In general, many carbohydrates such as glucose, maltose, mannose, sucrose, starch, glycerin, millet jelly, molasses, soy bean and the like can be used as sources of assimilable carbon. Sources of assimilable nitrogen include such materials as yeast and casein hydrolysates, primary yeast, yeast extracts, cottonseed flour, soybean solids, wheat germ meat extracts, peptone, corn steep liquor, and ammonium salts. The inorganic salt nutrients which can be incorporated in the culture medium are the customary salts yielding sodium, iron, magnesium, potassium, cobalt, phosphate and the like. In general, of course, the techniques employed will be chosen having regard to industrial efficiency. The growth media described herein are merely illustrative of the wide variety of media that may be employed and are not intended to be limiting.

Suitable growth media include (a) dextrose (20 g), yeast extract (5 g), soy flour (5 g), NaCl (5 g), $K_2HPO_4$ (5 g) and distilled water (1000 milliliters) where the pH is adjusted to 7.0 with aqueous HCl; (b) dextrin (10 g), beef extract (3 g), ardamine pH (5 g), N.Z amine type E (5 g), $MgSO_4.7H_2O$ (0.5 g), $KH_2PO_4$ (0.37 g), $CaCO_3$ (0.5 g), distilled water (1000 milliliters) where the pH is adjusted to 7.1 with aqueous HCl followed by a second stage of glucose (10 g), Hy-Case SF (2 g), beef extract (1 g), corn steep liquor (3 g), distilled water (1000 milliliters) where the pH is adjusted to 7.0; (c) glucose (10 g), corn steep liquor (6 g ), $KH_2PO_4$ (3 g), $CaCO_3$ (3.5 g), Soybean oil (crude, 2.2 milliliters), yeast extract (2.5 g), distilled water (1000 milliliters) where the pH is adjusted to 7.0–7.3 with aqueous HCl; (d) malt syrup (20 g), soybean meal (5 g), casein (1 g), dried yeast (1 g), NaCl (5 g), distilled water (1000 milliliters); (e) lactose (75 g), Pharmamedia (substitute yeast extract, 40 g), $CaCO_3$ (10 g), $Na_2SO_4$ (4 g), distilled water (1000 milliliters); (f) ISP#2; (g) ISP#3; (h) ISP#4; (i) ISP#5 and the like. The fermentation broth which is obtained thereby can be extracted with a suitable solvent such as ethyl acetate, methyl isobutylketone, methyl ethylketone, methylene chloride and the like, which removes the organic components from the fermentation broth. After extraction of the broth and evaporation of the solvent, the organic residue thus obtained is subjected to repeated chromatography to afford the three rapamycin analogs of the instant invention.

With respect to the macrolides of formulae (II), (III) and (IV) of this invention, it is to be understood that there are conformers or stereoisomeric forms such as optical and geometrical isomers due to asymmetric carbon atoms and double bonds, and such isomers are also included within the scope of this invention.

Rapamycin is prepared by the procedure described in U.S. Pat. No. 3,929,992, the disclosure of which is incorporated herein by reference.

The compounds of formulae (II) and (III) thus prepared are useful in the treatment of resistance to transplantation and autoimmune diseases such as rheumatoid arthritis or psoriasis. In the treatment of resistance to transplantation, a compound of formula (II) or (III) may be used either prophylactically or in response to an adverse reaction by the human subject to a transplanted organ or tissue. When used prophylactically, a compound of formulae (II) or (III) is administered to the patient or to the tissue or organ to be transplanted in advance of the transplantation operation. Prophylactic treatment may also include administration of the medication after the transplantation operation but before any signs of adverse reaction to transplantation are observed. When administered in response to an adverse reaction, a compound of formulae (II) or (III) is administered directly to the patient in order to treat said resistance to transplantation after outward signs of the resistance have been manifested.

The term "transplantation," when used above and hereinafter, refers to the implantation in one part of an individual of a tissue or organ taken from another part of that individual or from another individual. Typical transplantations include, but are not limited to, bone marrow, heart, renal, tendon and pancreaticoduodenal transplantations.

The term "graft," when used above and hereinafter, refers to any unattached tissue or organ which is used for transplantations. Typical grafts include, but are not limited to, skin, bone, fat and nerve grafts.

For use in the treatment of resistance to transplantation and autoimmune diseases such as rheumatoid arthritis or psoriasis in a mammal, including man, a compound of formula (II) or (III) is formulated into a suitable pharmaceutical composition containing a disease treating effective amount. Depending upon the potency of the particular compound of formulae (II) or (III) being administered, about 0.05 mg/kg of body weight per day to about 30 mg/kg of body weight per day, in single or multiple daily doses, is administered to the mammal being treated. A more preferred range is 0.05 mg/kg of body weight per day to about 20 mg/kg of body weight per day, although in particular cases, at the discretion of the attending physician, doses outside the broader range may be required. The preferred route of administration is generally oral, but parenteral administration (e.g., intravenous, intramuscular, subcutaneous or intramedullary) will be preferred in special cases such as where oral administration is inappropriate to the instant target or where the patient is unable for various reasons to ingest the drug. Topical administration may also be indicated, as where the patient is suffering from a skin disease such as psoriasis or whenever the medication is best applied to the surface of a tissue or organ as determined by the attending physician.

The compounds of formulae (II), (III) or (IV) thus prepared are also useful in the treatment of infections caused by fungi. For use in the treatment of said fungal infections in a mammal, including man, a compound of formula (II), (III) or (IV) is formulated into a pharmaceutical composition containing a disease treating effective amount. Depending upon the potency of the particular compound of formulae (II), (III) or (IV) being administered, about 0.05 mg/kg of body weight per day to about 30 mg/kg of body weight per day, in single or multiple daily doses, is administered to the mammal being treated. A more preferred range is 0.05 mg/kg of body weight per day to about 20 mg/kg of body weight per day, although in particular cases, at the discretion of the attending physician, doses outside the broader range may be required. The preferred route of administration is generally oral, but parenteral administration (e.g., intravenous, intramuscular, subcutaneous or intramedullary) will be preferred in special cases such as where oral administration is inappropriate to the instant target or where the patient is unable for various reasons to ingest the drug. Topical administration may also be indicated whenever the medication is best applied to the surface of a tissue or organ as determined by the attending physician.

For purposes of oral administration, tablets containing exdipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as, but not limited to, magnesium stearate, sodium lauryl sulfate and talc are often very useful for tableting purposes. Solid compositions of a similar type may also be employed as fillers in soft elastic and hard-filled gelatin capsules; preferred materials in this connection also include, by way of example and not of limitation, lactose or milk sugar as well as high molecular weight polyethylene glycols. When aqueous suspensions and/or elixirs are desired for oral administration, the essential active ingredient may be combined with various sweetening or flavoring agents, coloring matter or dyes and, if so desired, emulsifying and/or suspending agents, together with diluents such as water, ethanol, propylene glycol, glycerin and various like combinations thereof.

Although the generally preferred mode of administration of the compounds of this invention or its pharmaceutically-acceptable salts is oral, they may be administered parenterally as well. Such parenteral administration may be the preferred mode of administration for certain treatments.

For purposes of parenteral administration, solutions of a compound of this invention or a salt thereof in sesame or peanut oil or in aqueous propylene glycol may be employed. Such aqueous solutions should be suitably buffered if necessary, and the liquid diluent rendered isotonic with sufficient saline or glucose. These particular aqueous solutions are especially suitable for intravenous, intramuscular and subcutaneous injection purposes. In this connection, the sterile aqueous media employed are readily obtained by standard techniques well known to those skilled in the art. For instance, distilled water is ordinarily used as the liquid diluent and the final preparation is passed through a suitable bacterial filter such as a sintered glass filter or a diatomaceous-earth or unglazed porcelain filter. Preferred filters of this type include the Berkefeld, the Chamberland and the Asbestos Disk-Metal Seitz filter, wherein the fluid is sucked into a sterile container with the aid of a suction pump. The necessary steps should be taken throughout the preparation of these injectable solutions to insure that the final products are obtained in a sterile condition. For purposes of transdermal administration, the dosage form of the particular compound may include, by way of example, solutions, lotions, ointments, creams, gels, suppositories, rate-limiting sustained release formulations and devices therefor. Such dosage forms comprise the particular compound and may include ethanol, water, penetration enhancer and inert carriers such as gel-producing materials, mineral oil, emulsifying agents, benzyl alcohol and the like. Specific transdermal flux enhancing compositions are disclosed in European Patent Application 271,983 and European Patent Application 331,382, which have been filed in the name of the assignee of this invention, the teachings of which are incorporated herein by reference. For purposes of topical administration, the dosage form of the particular compound may include, by way of example and not of limitation, solutions, lotions, ointments, creams and gels. Further, administration by inhalation can be achieved by means and methods well known to those skilled in the art. Such means include the use of nebulizers or atomizers whereby a solution of a compound of this invention or a salt thereof is inhaled as a mist.

The utility of the compounds of the present invention as medical agents in the treatment of resistance to transplantation, fungal infectious diseases and autoimmune diseases such as rheumatoid arthritis or psoriasis is demonstrated by the activity of said compounds in the biological screens described hereinbelow. Said biological screen also provides a means whereby the activities of the compounds of formulae (II), (III) or (IV) can be compared with the activities of other known compounds. The results of these comparisons are useful for determining dosage levels in mammals, including man, for the treatment of resistance to transplantation and autoimmune diseases such as rheumatoid arthritis and psoriasis.

The human mixed lymphocyte reaction (MLR) is used to elicit a non-specific immune response which is measured via $^3$H-thymidine uptake. This screen uses peripheral blood mononuclear cells in a modified two-way MLR. To ensure disparity of HLA type D antigens and therefore maximize stimulation, a pool of frozen donor cells is used as the stimulator population; freshly isolated cells are used as the responder population.

Freshly drawn mononuclear cells are suspended in RPMI-1640 enriched with: 0.5% MEM non-essential amino acids (100x) solution, 1% L-glutamine (200 mM), 1% MEM vitamins (100x), 1% penicillin streptomycin solution (10,000 units/mL) and 15% heat-inactivated human AB serum (NABI). The cells are counted and the concentration is adjusted to 5x10$^5$ cells/mL. The solution is then transferred to round bottom 96 well plates in 100 μL/well quantities. These plates now contain the responder cells.

The stimulator cells are prepared by pooling the mononuclear cells collected from several different individuals. The cells are suspended in 90% human AB serum and 10% DMSO such that the cell count is 2x10$^7$ cells/mL. The cells are stored in liquid nitrogen. For an MLR, the viable cells are diluted to 5x10$^5$ cells/mL, and 100 μL/well is added to the plates containing the responder cells. To each well, containing a mixture of responder cells and stimulator cells, is added 50 μL of compound solution. Triplicate wells are run for each dose. The plates are incubated at 37° C. under an atmosphere of 5% $CO_2$ and are humidified for five days. To each well is added 1 μCi of $^3$H-thymidine and incubation is continued for another eighteen hours. The cells are harvested using the LKB Beta Plate system.

The percent inhibition of stimulated control is obtained using the following equation:

$$\% \text{ Inhibition} = \left[ 1 - \left( \frac{\text{avg. } cmp \text{ of drug}}{\text{avg. } cpm \text{ of stimulated control}} \right) \right] \times 100$$

The abbreviation cpm is defined as counts per minute. RPMI-1640 is a tissue culture medium which is available from Sigma.

Activity in the MLR screen recited above is indicative of usefulness of the active compound in the treatment of resistance to transplantation and autoimmune diseases such as rheumatoid arthritis and psoriasis.

Antimicrobial activities of the macrolides of the present invention against various fungi are determined by a serial agar dilution method in a Sabouraud agar. Minimum inhibitory concentrations (MIC) are obtained after incubation for 24 hours at 30° C.

The present invention is illustrated by the following examples. However, it should be understood that the invention is not limited to the specific details of these examples. Anhydrous solvents were used, anhydrous being defined as substantially free from water.

In the MLR protocol provided hereinabove, RPMI-1640 is a standard medium for MLR studies; MEM is defined as "minimum essential media"; and NABI is a supplier.

EXAMPLE ONE

Fermentation of Actinoplanes sp. ATCC 55586

Actinoplanes sp. ATCC No. 53771 was inoculated from slants into two 125 mL flasks containing 25 mL of growth medium. The composition of the growth medium was glucose (20 g/L), soy flour (5 g/L), yeast extract (5 g/L), NaCl (5 g/L), K$_2$HPO$_4$ (5 g/L) and the pH was adjusted to 7.0 with HCl. The inoculated seed medium was shaken at 28° C. for two days. The contents of the flasks were transferred to a Fernbach flask containing 500 mL of fresh growth medium of the same composition as recited hereinabove. After shaking the flask for one additional day, a sterile-filtered dimethyl sulfoxide solution of rapamycin (0.1 ml of a 100 mg/mL stock solution final concentration 0.4 mg/mL) was added. The fermentation was continued for two days, yielding a fermentation broth.

EXAMPLE TWO

Isolation of Compounds of Formulae (II), (III) and (IV)

The fermentation broth (about 500 mL) was extracted with an equal volume of ethyl acetate. The solvent was evaporated to afford 420 mg of an oil which was chromatographed on silica gel (eluted with ethyl acetate:hexane::3:1) to yield three fractions.

The first fraction (11.2 mg) was subjected to multiple prep HPLC (Zorbax SB CN —MeOH/H$_2$O gradient) to afford C-16-demethylrapamycin (the compound of formula (II), 1.5 mg). LSIMS m/e=922 (M+Na).

The second fraction (6.7 mg) was subjected to prep HPLC (Zorbax SB CN —MeOH/H$_2$O gradient) to yield C-39-demethylrapamycin (the compound of formula (III), 6.7 mg). LSIMS m/e=922 (M+Na).

The third fraction (24.5 mg) was chromatographed using prep HPLC (Zorbax SB CN —MeOH/H$_2$O gradient) to afford C-24-hydroxyrapamycin (the compound of formula (IV), 6.6 mg). $^1$H NMR (CDCl$_3$, δ): 0.70 (1H, q), 0.94 (3H, d), 0.98 (3H, d), 1.03 (1H, m), 1.14 (3H, d), 1.14 (1H, m), 1.24 (3H, d), 1.24 (1H, m), 1.33 (1H, m), 1.37 (1H, m), 1.40 (1H, m), 1.46 (1H, m), 1.50 (1H, m), 1.60 (1H, m), 1.60 (1H, m), 1.63 (2H, m), 1.66 (3H, s), 1.75 (3H, s), 1.76 (1H, m), 1.76 (1H, m), 1.80 (1H, m), 1.83 (1H, m), 1.85 (1H, m), 1.96 (1H, m), 2.02 (1H, m), 2.08 (1H, m), 2.17 (1 H, m), 2.31 (1H, m), 2.37 (1H, m), 2.67 (1H, dd), 2.73 (1H, dd), 2.96 (1H, m), 3.18 (3H, s), 3.24 (1H, m),3.32 (1H, m), 3.40 (1H, m), 3.40 (1H, m), 3.45 (3H, s), 3.45 (1H, m), 3.51 (1H, d), 3.63 (1H, m), 3.74 (1H, m), 3.76 (1H, d), 3.85 (1H, m), 4.21 (1H, d), 5.13 (1H, d), 5.30 (1H, m), 5.48 (1H, d), 5.57 (1H, dd), 5.95 (1H, d), 6.18 (1H, dd), 6.30 (1H, dd), 6.39 (1H, dd); LSIMS m/e 952 (M+Na).

We claim:

1. A compound according to the formula

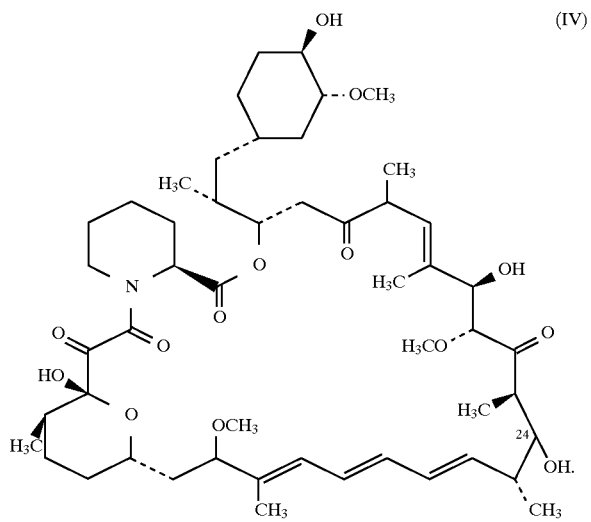

(IV)

2. A process for preparing a compound according to the formula

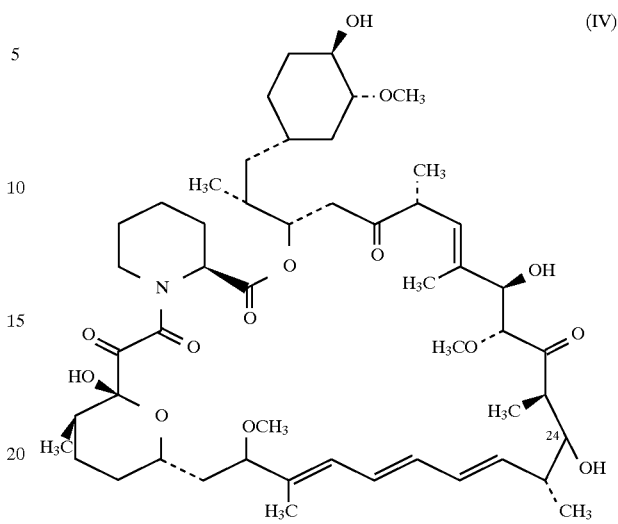

(IV)

comprising:

(a) fermenting Actinoplanes sp. ATCC 53771 in the presence of a compound of the formula

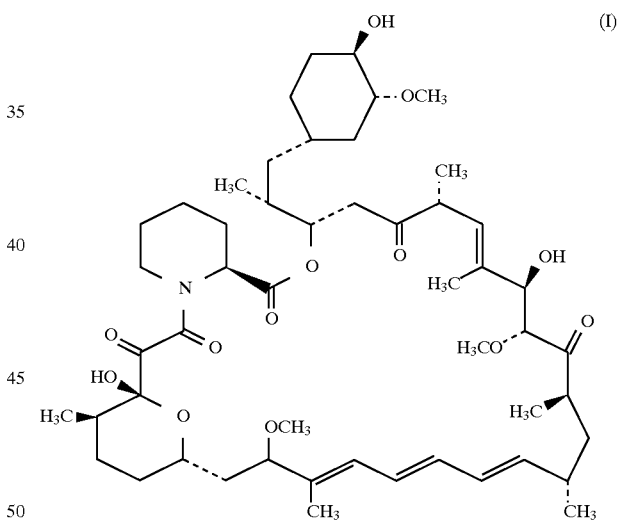

(I)

in a suitable growth medium and isolating said compound of formula (IV).

3. A method of treating a mammal suffering from a disease or condition caused by a fungus comprising administering to said mammal a fungal infectious disease treating a mount of a compound according to claim 1.

4. A pharmaceutical composition comprising the compound of claim 1 and a pharmaceutically acceptable carrier.

* * * * *